United States Patent
Valsesia et al.

(10) Patent No.: US 10,292,923 B2
(45) Date of Patent: May 21, 2019

(54) ALKOXY-SILANES COMPOUNDS AND RELATED CONDENSATION PRODUCTS AS COSMETIC RAW MATERIALS AND FOR COATING COSMETIC POWDERS

(71) Applicant: INTERCOS S.p.A., Milan (IT)

(72) Inventors: Patrizia Valsesia, Calco (IT); Gaetano Distefano, Bergamo (IT); Claudio Pirovano, Verderio (IT); Pietro Rando, Parzaniga (IT); Gabriele Depta, Monza (IT); Sara Bettinelli, Parabiago (IT)

(73) Assignee: INTERCOS S.P.A., Milan (IT)

( * ) Notice: Subject to any disclaimer, the term of this patent is extended or adjusted under 35 U.S.C. 154(b) by 12 days.

(21) Appl. No.: 15/573,586

(22) PCT Filed: Apr. 29, 2016

(86) PCT No.: PCT/IB2016/052450
§ 371 (c)(1),
(2) Date: Nov. 13, 2017

(87) PCT Pub. No.: WO2016/181251
PCT Pub. Date: Nov. 17, 2016

(65) Prior Publication Data
US 2018/0133136 A1      May 17, 2018

(30) Foreign Application Priority Data
May 14, 2015   (IT) .................. 102015000015176

(51) Int. Cl.
| | | |
|---|---|---|
| *A61K 8/58* | (2006.01) | |
| *C07F 7/18* | (2006.01) | |
| *A61K 8/02* | (2006.01) | |
| *A61K 8/11* | (2006.01) | |
| *A61Q 1/02* | (2006.01) | |
| *A61Q 1/06* | (2006.01) | |

(52) U.S. Cl.
CPC .............. *A61K 8/585* (2013.01); *A61K 8/022* (2013.01); *A61K 8/11* (2013.01); *A61Q 1/02* (2013.01); *A61Q 1/06* (2013.01); *C07F 7/1804* (2013.01); *C07F 7/1892* (2013.01); *A61K 2800/43* (2013.01); *A61K 2800/622* (2013.01); *A61K 2800/623* (2013.01); *A61K 2800/872* (2013.01)

(58) Field of Classification Search
None
See application file for complete search history.

(56) References Cited

U.S. PATENT DOCUMENTS

| | | | |
|---|---|---|---|
| 2013/0035400 A1 | 2/2013 | Nguyen et al. | |
| 2013/0036940 A1* | 2/2013 | Tanaka ..................... | C08L 1/02 106/200.3 |

FOREIGN PATENT DOCUMENTS

| | | | | |
|---|---|---|---|---|
| EP | 2 236 125 | 10/2010 | | |
| EP | 2236125 A1 * | 10/2010 | ............... | A61K 8/25 |

OTHER PUBLICATIONS

International Search Report dated Dec. 12, 2016 in International Application No. PCT/IB2016/052450.
Written Opinion of the InternationaL Searching Authority dated May 19, 2017 in International Application No. PCT/IB/2016/052450.
International Preliminary Report on Patentability dated May 19, 2017 in International Application No. PCT/IB/2016/052450.

* cited by examiner

*Primary Examiner* — Clinton A Brooks
*Assistant Examiner* — Kofi Adzamli
(74) *Attorney, Agent, or Firm* — Wenderoth, Lind & Ponack, L.L.P.

(57) ABSTRACT

There are described alkoxy-silanes compounds and related condensation products as cosmetic raw materials and for coating cosmetic powders; synthesis processes of such compounds and condensation products and production of coated cosmetic powders. Said cosmetic powders can be used for preparing cosmetic products such as anhydrous products for face/eyes/lips, cosmetic pencils and face/eyes emulsions.

15 Claims, No Drawings

ALKOXY-SILANES COMPOUNDS AND RELATED CONDENSATION PRODUCTS AS COSMETIC RAW MATERIALS AND FOR COATING COSMETIC POWDERS

The present invention relates to alkoxy-silanes compounds and related condensation products as cosmetic raw materials and for coating cosmetic powders.

Cosmetic products allow the appearance of the skin to be improved by modifying the optical properties of the skin and imparting a desired appearance thereto (decoration, wrinkle masking, complexion evening effect, flaw covering, such as stains and pathological or physiological skin lesions).

These optical modifications work by changing the light absorption and/or scattering by the user's skin by means of a layer of cosmetic material applied, depending on the formulation used, in the form of dispersion, lotion, emulsion or powder.

In most of the cases contemplated in decorative cosmetics, such optical modifications are obtained by means of colored powders (pigments and/or pearls) in combination with white powders (actually transparent, such as excipients and touch modifiers).

The decorative film applied by means of the cosmetic formulation represents a foreign object deposited on a functional and highly specialized organ as the skin is, and therefore limiting the alterations to the skin physiology due to the cosmetic formulation is essential.

In particular, powdery cosmetic ingredients widely used in the art (such as pigments and excipients), due to their reduced particle size and high specific surface area, cause the absorption of cutaneous lipids and moisture and therefore an inevitable alteration of the protective hydrolipidic film produced by the skin, which is therefore depleted. The result of such an alteration is the occurrence of adverse symptoms such as dry skin, loss of elasticity and tone.

In fact, the outer layer of skin, referred to as stratum corneum, consists of a series of differentiated laminated non-viable cell layers of a protein nature (corneocytes) immersed in a hydrolipidic matrix consisting of ceramides, fatty acids, mineral salts, amino acids and water. To ensure adhesion and affinity between the corneocytes and the hydrolipidic matrix in which they are immersed, there is the presence of ceramides covalently anchored to the surface of the corneocytes themselves ($\omega$-hydroxyceramides, see Macheleidt, o. et al. (2002) "Deficiency of epidermal protein-bound omega-hydroxyceramides in atopic dermatitis" J. Invest. Dermatol. 119, 166-173 and Behne, M. et al, (2000) Omega-hydroxyceramides are required for corneocyte lipid envelope (CLE) formation and normal epidermal permeability barrier function" J. Invest. Dermatol. 114, 185-192.): this functionalization is believed to improve the interface and the continuity of the whole epidermis, thus promoting the physiological functions thereof (mechanical elasticity, homeostasis, barrier against perspiration, protection against microorganism attacks, etc.), making the skin a real composite biomaterial.

The invention of cosmetic powders protecting the balance of the epidermis, mimicking the chemical structure thereof, is a requirement and an improvement compared to what is available in the art.

WO 2014084657 describes a polymeric coating with quaternary ammonium and phosphate covalently anchored to the surface of titanium dioxide and sericite to promote the adhesion of said powders to the skin. Disadvantageously, the absence of fatty features mimicking the composition of the lipid layer does not ensure the effective biomimicry.

JP 2000290532 describes a preparation of cosmetic powders with greater skin affinity by means of the physical deposition of N-lauroyl-L-lysine (a fatty amino acid) by simple precipitation, without the formation of covalent bonds between the powder surface and the coating, which undermines the stability thereof in complex formulations.

KR 1446500 describes a preparation of coated powders with improved skin affinity by means of treatment of inorganic substrates with lipid mixtures equivalent to those present in the epidermis, without the formation of covalent bonds between substrate and coating.

JP 2014088350 describes cosmetic powders coated with alkoxy-silanes which ensure the covalent attachment of the coating to the powder, but without providing fatty functionalities and molecular weight similar to that of the epidermal lipids, essential for an effective barrier effect against perspiration.

It is the object of the present invention to obtain cosmetic powders with the surface features of the skin corneocytes, therefore capable of self-integrating seamlessly with the stratum corneum.

It is a further object to obtain powders which protect the balance of the epidermis, mimicking the chemical structure thereof. Therefore, a first object of the present invention are organic compounds for coating powders for cosmetic use.

Said coating compounds have both hydrophobic features and polar features, i.e. are able to form or participate in hydrogen bonds, similar to what happens in the epidermal lipids.

The coating compounds of the present invention can be subjected to hydrolysis and condensation reaction. Said compounds have fatty functionalities and at the same time donor-acceptor capacity for hydrogen bonds (urethane/ureic groups), similarly to the amide groups of the epithelial lipids.

Such skin-friendly coating compounds have general formula (1):

where:

A is a hydrocarbon radical having from 10 to 100 carbon atoms.

More preferably, A is a hydrocarbon radical having from 15 to 25 carbon atoms and formally derived from an AX precursor with X=—OH or —NH$_2$, with melting and softening point higher than 25° C. and lower than 100° C. Such hydrocarbon radical A may be linear, branched or cyclic, and moreover it may be saturated or mono- or polyunsaturated or comprise aromatic rings, moreover, it may have branches containing polar groups, ionic or ionizable groups;

B may be a ureic/urethane group, more preferably a urethane group of formula (2):

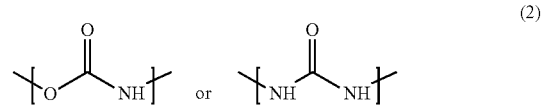

and C is a propyl trialkoxyl silane group —(CH$_2$)$_3$Si(OR$^1$)$_x$(OR$^2$)$_{3-x}$ where 0≤x≤3 (3):

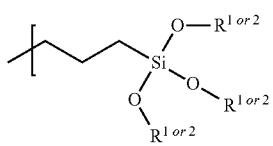

(3)

where $R^1$ is an ethyl radical —$CH_2CH_3$ and $R^2$ is the methyl radical —$CH_3$. The skin-friendly organic coating compound according to the general formula 1 can be synthesized starting from commercially available reagents.

In a practical embodiment, the general formula 1 can be obtained by reacting the 3-isocyanatepropyltriethoxysilane compound (4) (CAS #24801-88-5, available from Wako Pure Chemical Industries, Ltd., Osaka, Japan, TCI Europe N.V., Zwijndrecht, Belgium or Gelest, Inc. Morrisville, Pa., United States)

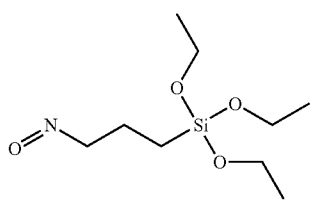

(4)

with an equimolar amount of 1-docosanol (INCI: Behenyl Alcohol) (CAS #661-19-8, available from Acros Organics, Geel, Belgium, Sigma-Aldrich, St. Louis, Mo., United States or Merck KGaA, Darmstadt, Germany), in anhydrous decane at a temperature of 80° C. for 6 hours and in the presence of a suitable catalyst of the addition reaction—as known in the art—to obtain an intermediate docosanil carbamoyl propyl triethoxysilane compound (5):

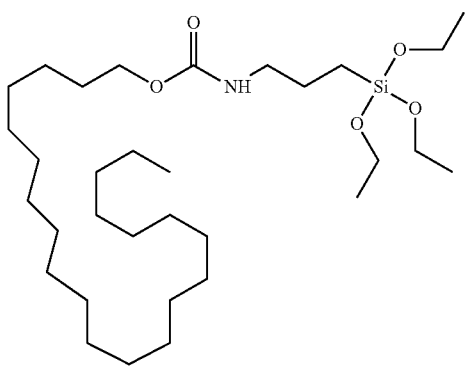

(5)

The intermediate compound (5) can be purified in the form of white waxy solid from the reaction environment by crystallization, filtration and drying.

The coating compounds of general formula (1) can undergo a sol-gel process, i.e. hydrolysis and condensation reactions for the surface modification of cosmetic powders, thereby creating yielding cosmetic powders having a high adhesion capacity with texturizing, lubricant and mat finishing functions.

Such hydrolysis and condensation reactions of the coating compounds (1) lead to obtain cosmetic powders with a strong adherence to the skin and naturalness, due to the chemical compatibility of the fatty and polar functionalities imparted by the subject powder to the cosmetic formulation.

Said condensation product, in the form of fine powder, is provided with cosmetic properties such as hydrophobicity, as it does not detract moisture from the skin, adhesion since it is adapted to form a film adhered to the skin; transparency, as it creates a translucent powder film and gives a natural look to the skin; softness and smoothness by generating pleasant sensations during the application.

A first embodiment for producing cosmetic powders starting from compound (5) at 10% by weight in 1:1 ethanol: isododecane mixture, subjected to acid or basic catalysis, produces the organic-inorganic hybrid compound, obtained by polycondensation of compound (5), having structure:

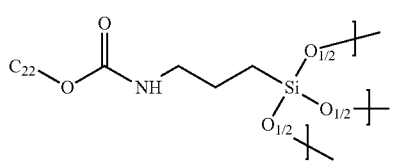

(6)

Such a solid compound (6) can be purified from the condensation environment by filtration, drying and possible grinding, obtaining a powdery solid having a particle size <500 μm, more preferably <250 μm, even more preferably <100 μm, which when added to a cosmetic formulation from 80 to 1%, more preferably from 50 to 5%, even more preferably from 30 to 10%, imparts desirable cosmetic properties in said formulation.

A second embodiment for producing cosmetic powders requires that the polycondensation reaction is carried out in the presence of a suitable cosmetic substrate. The resulting functional powder permanently adopts new surface features attributable to the polycondensed compound. In fact, the need to impart new surface properties to cosmetic powders requires a stable chemical modification between the coating agent and the powder itself.

The grafting by means of sol-gel chemistry of the coating on the substrate allows to select a wide variety of cosmetic substrates provided with surface hydroxyls (silicates, silica, alumina, aluminum hydroxide, titanium, perlite) and functionalize them through the formation of stable covalent bonds (Si—O bond, 452 kJ/mol) with a coating agent (up to 3 covalent bonds per coating molecule).

Such a chemical coating is achieved, for example, by nebulizing from 1 to 10% of intermediate compound (5) on talcum powder, more preferably from 2 to 5% by weight with respect to talc, conveying the compound by means of a suitable solution in volatile organic solvents (e.g. ethanol, isopropanol, ethyl acetate, isododecane or mixtures thereof). The addition of an acid (e.g. diluted HCL) or basic (e.g. NaOH) solution allows the reaction as shown:

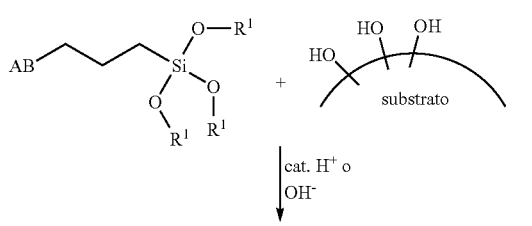

(7)

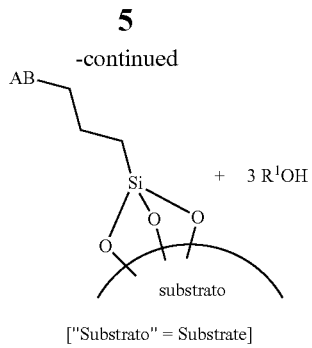

["Substrato" = Substrate]

The powder thus obtained, after intensive mixing, is subjected to drying in oven at temperatures from 50° C. to 150° C., more preferably from 80° C. to 100° C. for 2 hours to 48 hours, more preferably more than 24 hours.

Alternatively, in a different embodiment, such a cosmetic powder can be obtained by dry mixing (without solvent) compound (1) with the cosmetic substrate by means of ploughshare mills heated to the melting temperature of the coating, followed by acid or basic catalysis and temperature treatment for 2 hours to 48 hours, more preferably more than 4 hours.

EXAMPLES

The following examples are intended to clarify the present invention without limiting it in any way.

Example 1

Preparation of a "Coating Phase" Obtained by Reaction with a Linear Alcohol

| | Name | % (w/w) |
|---|---|---|
| Phase A | 3-(triethoxysilyl)propylisocyanate, 95% | 43.870 |
| | 1-docosanol | 55.030 |
| | Zinc stearate | 0.100 |
| Phase B | Ethanol | 1.000 |

The present coating phase is prepared by placing phase A in a reactor provided with stirrer, thermometer and condenser. The reaction is carried out under nitrogen flow, heating the mass to a temperature of 90° C. for about 10 hours up to the disappearance of the active isocyanate groups. This disappearance is evaluated by IR. Phase B is subsequently added at about 70° C.

The product thus obtained has a whitish waxy consistency with a melting point of about 60° C.

Example 2

Preparation of a "Coating Phase" Obtained by Reaction with a Branched Alcohol

| | Name | % (w/w) |
|---|---|---|
| Phase A | 3-(triethoxysilyl)propylisocyanate, 95% | 35.360 |
| | Tetradecyloctadecanol | 63.540 |
| | Zinc stearate | 0.100 |
| Phase B | Ethanol | 1.000 |

The present coating phase is prepared by following the procedure shown in Example 1.

The product thus obtained has a whitish waxy consistency with a melting point of about 35° C.

Example 3

Preparation of a "Coating Phase" Obtained by Reaction with a Partially Esterified Glycol

| | Name | % (w/w) |
|---|---|---|
| Phase A | 3-(triethoxysilyl)propylisocyanate, 95% | 27.830 |
| | C20-30 Glycol Isostearate | 71.070 |
| | Zinc stearate | 0.100 |
| Phase B | Isopropyl alcohol | 1.000 |

The present coating phase is prepared by following the procedure shown in Example 1.

The product thus obtained has a whitish waxy consistency with a melting point of about 55° C.

Example 4

Preparation of a "Coating Phase" Obtained by Reaction with an Amphiphilic Zwitterionic Molecule

| | Name | % (w/w) |
|---|---|---|
| Phase A | 3-(trimethoxysilyl)propylisocyanate, 95% | 16.107 |
| | Lauryl Hydroxysultaine | 82.793 |
| | Zinc stearate | 0.100 |
| Phase B | Isopropyl alcohol | 1.000 |

The present coating phase is prepared by following the procedure shown in Example 1.

The product thus obtained has a whitish waxy consistency with a softening point of about 37° C.

Example 5

Preparation of a Coated Cosmetic Powder

| | Name | % (w/w) |
|---|---|---|
| Phase A | Talc | 89.500 |
| Phase B | Coating phase obtained in example 1, 2, 3, 4 | 1.790 |
| | Ethanol | 3.480 |
| | Isododecane | 3.480 |
| Phase C | Hydrochloric acid solution (1.42N) | 1.750 |

The coated cosmetic powder of the example was obtained by loading phase A in a mixer and stirring it with a suitable impeller, phase B and phase C were atomized in sequence on the powder of phase A at room temperature. The wet powder is then unloaded into suitable containers and dried in an oven at 80° C. for 24 hours. The volatile contents after oven treatment should be <1%. Finally, the powder is sifted with a 200 mesh sieve. The surface tension of such a coated powder is 35.4 dyne/cm.

The powder selected for this example is in no way limiting with respect to all the other cosmetic powders that may be used (mica, silica, etc.).

Example 6

Preparation of a Coated Cosmetic Pigment

|         | Name                                    | % (w/w) |
|---------|-----------------------------------------|---------|
| Phase A | Red iron oxide                          | 89.500  |
| Phase B | Coating phase obtained in example 1, 2, 3, 4 | 1.790 |
|         | Ethanol                                 | 3.480   |
|         | Isododecane                             | 3.480   |
| Phase C | Hydrochloric acid solution (1.42N)      | 1.750   |

The coated cosmetic pigment of the example was obtained by loading phase A in a mixer and stirring it with a suitable impeller, phase B and phase C were atomized in sequence on the pigment of phase A at room temperature. The wet powder is then unloaded into suitable containers and dried in an oven at 80° C. for 24 hours. The volatile contents after oven treatment should be <1%. Finally, the pigment is sifted with a 200 mesh sieve. The surface tension of such a coated pigment is 33.9 dyne/cm.

The pigment selected for this example is in no way limiting with respect to all the other cosmetic pigments that may be used (Titanium dioxide, Yellow iron oxide, Black iron oxide, etc.).

Example 7

Preparation of a Coated Cosmetic Pigment

|         | Name                                    | % (w/w) |
|---------|-----------------------------------------|---------|
| Phase A | Red 7 lake                              | 87.360  |
| Phase B | Coating phase obtained in example 1, 2, 3, 4 | 3.930 |
|         | Ethanol                                 | 3.480   |
|         | Isododecane                             | 3.480   |
| Phase C | Hydrochloric acid solution (1.42N)      | 1.750   |

The coated cosmetic pigment of the example was obtained by loading phase A in a mixer and stirring it with a suitable impeller, phase B and phase C were atomized in sequence on the pigment of phase A at room temperature. The wet powder is then unloaded into suitable containers and dried in an oven at 80° C. for 24 hours. The volatile contents after oven treatment should be <1%. Finally, the pigment is sifted with a 200 mesh sieve. The surface tension of such a coated pigment is 35.4 dyne/cm.

The pigment selected for this example is in no way limiting with respect to all the other cosmetic pigments, in the form of lakes, that may be used (Blue 1 lake, Yellow 5 lake, etc.).

Example 8

Preparation of a Colored Cosmetic Emulsion

|         | Name            | % (w/w) |
|---------|-----------------|---------|
| Phase A | Isododecane     | 33.900  |
|         | Water           | 43.800  |
|         | Glycerin        | 2.000   |
|         | Butylene glycol | 3.000   |
|         | Squalane        | 1.000   |
|         | Glyceryl oleate | 1.000   |

-continued

|         | Name                                    | % (w/w) |
|---------|-----------------------------------------|---------|
| Phase B | Disteardimonium hectorite               | 1.800   |
|         | Propylene carbonate                     | 0.600   |
|         | Titanium dioxide coated as in example 6 | 8.000   |
|         | Red iron oxide coated as in example 6   | 0.500   |
|         | Yellow iron oxide coated as in example 6 | 2.800  |
|         | Black iron oxide coated as in example 6 | 0.200   |
| Phase C | Preservatives                           | 1.400   |

Example 9

Preparation of a Pressed Powder Foundation

|         | Name                                    | % (w/w) |
|---------|-----------------------------------------|---------|
| Phase A | Talc coated as in example 5             | 75.000  |
|         | Mica coated as in example 5             | 5.200   |
|         | Titanium dioxide coated as in example 6 | 1.000   |
|         | Red iron oxide coated as in example 6   | 0.600   |
|         | Yellow iron oxide coated as in example 6 | 2.000  |
|         | Black iron oxide coated as in example 6 | 0.200   |
|         | Spherical silica coated as in example 5 | 10.700  |
|         | Nylon-12                                | 5.000   |
| Phase B | Preservatives                           | 0.300   |

Example 10

Preparation of a Lipstick

|         | Name                                              | % (w/w) |
|---------|---------------------------------------------------|---------|
| Phase A | Microcrystalline wax                              | 25.000  |
|         | Diisostearyl malate                               | 48.650  |
|         | Hydrogenated styrene/methyl styrene/indene copolymer | 10.600 |
| Phase B | Titanium dioxide coated as in example 6           | 1.800   |
|         | Red 7 lake coated as in example 7                 | 0.700   |
|         | Yellow 5 lake coated as in example 7              | 2.700   |
|         | Blue 1 lake coated as in example 7                | 0.250   |
|         | Caprylic/capric triglyceride                      | 10.000  |
| Phase C | Preservatives                                     | 0.300   |

Example 11

Preparation of a Cosmetic Pencil

|         | Name                                 | % (w/w) |
|---------|--------------------------------------|---------|
| Phase A | Octyldodecanol                       | 48.000  |
|         | Polyethylene                         | 23.000  |
|         | Hydrogenated polyisobutene           | 5.600   |
|         | Isohexadecane                        | 8.900   |
| Phase B | Disteardimonium hectorite            | 0.900   |
|         | Propylene carbonate                  | 0.300   |
|         | Mica coated as in example 5          | 0.800   |
|         | Yellow 5 lake coated as in example 7 | 1.500   |
|         | Blue 1 lake coated as in example 7   | 10.700  |
| Phase C | Preservatives                        | 0.300   |

The invention claimed is:

1. A skin-friendly coating compound for the surface modification of cosmetic powders using sol-gel chemistry of general formula:

A-B—C  (1)

where:
A is a hydrocarbon radical having from 10 to 100 carbon atoms and formally derived from an AX precursor with X=—OH or —NH$_2$, with melting or softening point higher than 25° C. and lower than 100° C.,
B is a ureic or urethane group of formula:

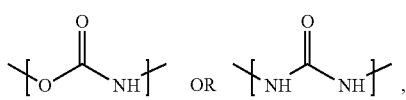  (2)

C is a propyl trialkoxyl silane group —(CH$_2$)$_3$Si(OR$^1$)$_x$(OR$^2$)$_{3-x}$ where 0≥x≥3 of formula (3)

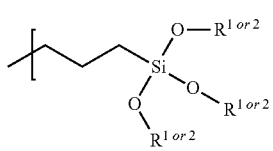  (3)

where R$^1$ corresponds to an ethyl radical —CH$_2$CH$_3$ and R$^2$ to the methyl radical —CH$_3$.

2. A coating compound for cosmetic powders according to claim 1, wherein
A is a hydrocarbon radical having from 15 to 25 carbon atoms,
B is a urethane group,
C is a propyl trialkoxyl silane group —(CH$_2$)$_3$Si(OR$^1$)$_x$(OR$^2$)$_{3-x}$ where 0≥x≥3 where R$^1$ corresponds to an ethyl radical —CH$_2$CH$_3$ and R$^2$ to the methyl radical —CH$_3$.

3. A coating compound for cosmetic powders according to claim 1, wherein said organic compound is the docosanil carbamoyl propyl triethoxysilane compound of formula (5)

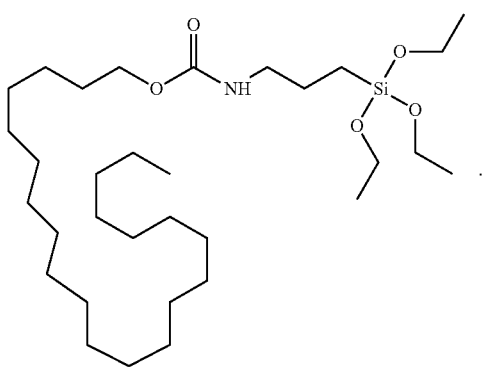  (5)

4. Coating compound for cosmetic powders, according to claim 1, obtained by reacting 3-isocyanatepropyltriethoxysilane compound of formula (4)

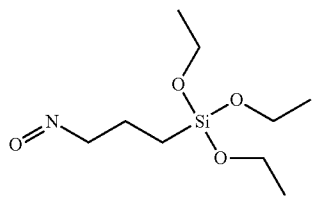  (4)

with an equimolar amount of an AX compound, in anhydrous decane at a temperature of 70-95° C. for 6-10 hours and in the presence of a catalyst of the addition reaction, the purification of the organic compound in the form of white waxy solid from the reaction environment via crystallization, filtration and drying, characterized in that said coating compound is in a 10% percentage by weight in 1:1 ethanol: isododecane mixture, subjected to acid or base catalysis, adapted to obtain the organic-inorganic hybrid compound by condensation of formula (6)

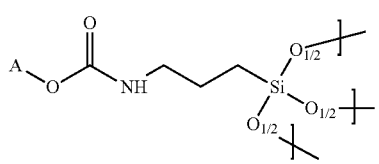

said organic-inorganic hybrid compound being adapted to be purified by filtration, drying and possible grinding to obtain a powdery solid having a particle size of <500 μm.

5. Coating compound according to claim 4, wherein the grinding is adapted to obtain a powdery solid having a particle size of <250 μm.

6. Coating compound according to claim 4, wherein the grinding is adapted to obtain a powdery solid having a particle size of <100 μm.

7. Coating compound according to claim 4, wherein the powdery solid is adapted to be added to a cosmetic formulation in a percentage from 80% to 1%.

8. Coating compound according to claim 7, wherein the powdery solid is adapted to be added to a cosmetic formulation in a percentage from 50% to 5%.

9. Coating compound according to claim 7, wherein the powdery solid is adapted to be added to a cosmetic formulation in a percentage from 30% to 10%.

10. Coating compound according to claim 4, wherein the condensation reaction occurs in the presence of a suitable cosmetic substrate comprising surface silanols adapted to be functionalized through the formation of stable covalent bonds with the organic compound.

11. Coating compound according to claim 1, wherein it comprises the docosanil carbamoyl propyl triethoxysilane compound from 1 to 10% by weight with respect to a cosmetic substrate, conveying the compound by means of an appropriate solution in volatile organic solvents, adding an acid or basic solution for obtaining a cosmetic powder being adapted to be subjected to drying in oven at temperatures from 50° C. to 150° C. for 2-48 hours.

12. Coating compound according to claim 11, wherein it comprises the docosanil carbamoyl propyl triethoxysilane compound from 2 to 5% and in that said production process takes place at 80 to 100° C. for more than 24 hours.

13. A method of using the coating compound according to claim 1 for coating a cosmetic powder intended to the formation of a pressed powder foundation.

14. A method of using the coating compound according to claim 1 for coating a cosmetic powder intended to the formation of a lipstick.

15. A method of using the coating compound according to claim 1 for coating a cosmetic powder intended to the formation of a cosmetic pencil.

\* \* \* \* \*